(12) United States Patent
Maubru

(10) Patent No.: US 7,498,022 B2
(45) Date of Patent: Mar. 3, 2009

(54) COSMETIC COMPOSITION COMPRISING AT LEAST ONE ANIONIC SURFACTANT, AT LEAST ONE CATIONIC POLYMER AND AT LEAST ONE AMPHIPHILIC, BRANCHED BLOCK ACRYLIC COPOLYMER AND METHOD FOR TREATING HAIR USING SUCH A COMPOSITION

(75) Inventor: Mireille Maubru, Chatou (FR)

(73) Assignee: L'Oreal S.A.

( * ) Notice: Subject to any disclaimer, the term of this patent is extended or adjusted under 35 U.S.C. 154(b) by 912 days.

(21) Appl. No.: 10/400,570

(22) Filed: Mar. 28, 2003

(65) Prior Publication Data

US 2003/0223948 A1 Dec. 4, 2003

Related U.S. Application Data

(60) Provisional application No. 60/394,719, filed on Jul. 10, 2002.

(30) Foreign Application Priority Data

Mar. 28, 2002 (FR) .................................. 02 03955

(51) Int. Cl.
*A61Q 5/02* (2006.01)
(52) U.S. Cl. ............... 424/70.13; 424/70.11; 424/70.15
(58) Field of Classification Search ........................ None
See application file for complete search history.

(56) References Cited

U.S. PATENT DOCUMENTS

| | | | |
|---|---|---|---|
| 2,261,002 A | 10/1941 | Ritter et al. |
| 2,271,378 A | 1/1942 | Searle et al. |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer et al. |
| 2,781,354 A | 2/1957 | Mannheimer et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,131,576 A | 12/1978 | Iovine et al. |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,591,610 A | 5/1986 | Grollier |

(Continued)

FOREIGN PATENT DOCUMENTS

| | | |
|---|---|---|
| EP | 0 122 324 B1 | 1/1988 |
| EP | 0 122 324 B2 | 3/1993 |
| EP | 0 337 354 B1 | 2/1994 |
| WO | WO95/09599 * | 4/1995 |
| WO | WO 00/40628 | 7/2000 |
| WO | WO 01/05365 A1 | 1/2001 |
| WO | WO 01/19946 | 3/2001 |
| WO | WO 01/96429 A1 | 12/2001 |

OTHER PUBLICATIONS

Lubrizol Technical Data Sheet (Jan. 9, 2003).*

(Continued)

*Primary Examiner*—Jyothsna A Venkat
(74) *Attorney, Agent, or Firm*—Finnegan, Henderson, Farabow, Garrett & Dunner, LLP

(57) ABSTRACT

A cosmetic composition comprising, in a cosmetically acceptable medium,
at least one amphiphilic polymer chosen from branched block copolymers comprising
(a) at least one nonionic unit derived from at least one monomer chosen from $C_{1-20}$ alkyl (meth)acrylates, N-mono-($C_{2-12}$ alkyl)-(meth)acrylamides and N,N-di-($C_{2-12}$ alkyl)-(meth)acrylamides,
(b) at least one anionic unit derived from at least one monomer chosen from acrylic acid and methacrylic acid, and
(c) at least one polyfunctional unit derived from at least one monomer comprising at least two polymerizable unsaturated functional groups,
at least one cationic polymer, and
at least 3% by weight, relative to the total weight of the composition, of at least one anionic surfactant, and a method for treating a keratinous material using the composition.

24 Claims, No Drawings

U.S. PATENT DOCUMENTS

| | | |
|---|---|---|
| 4,608,250 A | 8/1986 | Jacquet et al. |
| 4,719,099 A | 1/1988 | Grollier et al. |
| 4,761,273 A | 8/1988 | Grollier et al. |
| 4,803,221 A | 2/1989 | Bair |
| 4,839,166 A | 6/1989 | Grollier et al. |
| 4,948,579 A | 8/1990 | Jacquet et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,196,189 A | 3/1993 | Jacquet et al. |
| 5,391,368 A | 2/1995 | Gerstein |
| 5,656,257 A | 8/1997 | Fealy et al. |
| 5,958,392 A | 9/1999 | Grollier et al. |
| 6,383,995 B1 | 5/2002 | Maurin et al. |
| 6,635,702 B1 * | 10/2003 | Schmucker-Castner et al. .. 524/291 |
| 2002/0086038 A1 | 7/2002 | Belli |

OTHER PUBLICATIONS

Porter, M.R., "Nonionics", Handbook of Surfactants, Chapter 7, 1991, pp. 116-178.

"Fixate™" G100 Hair Fixative Polymer Technical Data Sheet, Lubrizol, Technical Data Sheet - 298, Jan. 9, 2003.

French Search Report for FR0203955 (Priority Application).

English language Derwent abstract for EP 0 080 976.

English language Derwent abstract for FR 2 336 434.

* cited by examiner

COSMETIC COMPOSITION COMPRISING AT LEAST ONE ANIONIC SURFACTANT, AT LEAST ONE CATIONIC POLYMER AND AT LEAST ONE AMPHIPHILIC, BRANCHED BLOCK ACRYLIC COPOLYMER AND METHOD FOR TREATING HAIR USING SUCH A COMPOSITION

This application claims benefit of U.S. Provisional Application No. 60/394,719, filed Jul. 10, 2002.

Disclosed herein is a cosmetic composition comprising at least one anionic surfactant, at least one amphiphilic polymer chosen from branched block acrylic copolymers, and at least one conditioning agent chosen from cationic polymers. Further disclosed herein is a method for treating hair using such a composition.

Although a very large number of fixing polymers are known in the field of hair-styling, most of them may have, for example, a limited fixing power when they are used in rinse-out hair compositions such as shampoos or conditioners.

The very advantageous hair-styling properties of a group of amphiphilic, branched, block acrylic copolymers which have a structure wherein blocks of relatively hydrophilic acrylic monomers are attached to a block of acrylic monomers which is relatively more hydrophobic than the blocks which it carries have been recently discovered. These novel amphiphilic, branched, block copolymers are described in International Patent Application Nos. WO 00/40628 and WO 01/96429.

International Patent Application Nos. WO 00/40628 and WO 01/96429 describe the structure of these novel polymers and a method for preparing them and their use in the hair-styling field in the form of leave-in hair-styling compositions such as hair-styling lacquers and mousses in the form of aerosol compositions comprising organic solvents and propelling agents.

The inventor has discovered that the amphiphilic, branched, block acrylic copolymers disclosed in the above-mentioned International patent applications could also be used in rinse-out compositions if they were combined with at least one cationic polymer and with at least one anionic surfactant.

Indeed, the introduction, into at least one anionic surfactant base, of the combination of at least one cationic polymer and at least one amphiphilic polymer chosen from branched, block copolymers as described below can give rise to shampoos which have excellent hair-styling properties and which can confer good cosmetic properties on the hair, for example, sleekness and gloss.

The good results obtained with the combination of the polymers disclosed herein were not predictable because the use of cationic polymers in combination with anionic polymers in a surfactant base to provide a hair-styling effect has, up until now, not allowed satisfactory cosmetic properties to be obtained, for example, hair sleekness and gloss.

The compositions disclosed herein may also, for example, be used on the skin. They then make it possible to obtain very good conditioning properties.

Disclosed herein is a cosmetic composition comprising, in a cosmetically acceptable medium,
  at least one amphiphilic polymer chosen from branched block copolymers comprising:
    (a) at least one nonionic unit derived from at least one monomer chosen from $C_1$-$C_{20}$ alkyl(meth)acrylates, N-mono-($C_2$-$C_{12}$ alkyl)-(meth)acrylamides and N,N-di-($C_2$-$C_{12}$ alkyl)-(meth)acrylamides,
    (b) at least one anionic unit derived from at least one monomer chosen from acrylic acid and methacrylic acid, and
    (c) at least one polyfunctional unit derived from at least one monomer comprising at least two polymerizable unsaturated functional groups, and, for example, having a structure comprising at least one hydrophilic block, attached to at least one hydrophobic block, via the at least one polyfunctional unit (c),
  at least one cationic polymer, and
  at least 3% by weight, relative to the total weight of the composition, of at least one anionic surfactant.

Also disclosed herein is a method for treating a keratinous material comprising applying to the keratinous material the composition disclosed herein and, after an optional exposure time, rinsing the keratinous material.

The exposure time for the composition may range, for example, from 0 seconds to 30 minutes.

The at least one amphiphilic polymer chosen from branched block copolymers disclosed herein and its preparation are disclosed in International Patent Application Nos. WO 00/40628 and WO 01/96429, which are incorporated herein by reference.

The at least one amphiphilic polymer may comprise, for example, a macromolecular structure wherein at least one relatively hydrophilic sequence, comprising at least one anionic monomer, is attached via the at least one polyfunctional unit (for example at least one unit comprising at least two polymerizable carbon-carbon double bonds) to at least one relatively more hydrophobic block.

The at least one amphiphilic polymer is obtained by a method of polymerization in two stages: in a first stage, monomers or a mixture of monomers, which are relatively hydrophobic, are polymerized in the presence of at least one polyfunctional comonomer comprising at least two polymerizable functional groups having different reactivities. In this first stage, the hydrophobic monomers polymerize by reacting with the most reactive functional group of the at least one polyfunctional comonomer so as to form a copolymer chain comprising a certain number of polymerizable groups corresponding to less reactive groups of the at least one polyfunctional comonomer. In a second stage, the copolymer chain comprising the polymerizable groups, which is obtained in the first stage, is reacted with monomers or a mixture of monomers, which are relatively more hydrophilic, of which a certain fraction comprises carboxylic acid groups. These relatively more hydrophilic monomers polymerize by reacting with the polymerizable groups of the hydrophobic copolymer chain so as to form relatively more hydrophilic blocks, attached in the form of branches to this first copolymer chain.

As explained in International Patent Application Nos. WO 00/40628 and WO 01/96429, the sequences forming these branched acrylic copolymers do not only differ in their more or less hydrophobic character, but also in their glass transition temperatures. Indeed, the relatively more hydrophilic sequences are so-called "hard" sequences because they have a glass transition temperature greater than room temperature (defined herein as 20° C.), whereas the relatively more hydrophobic sequences are so-called "soft" sequences because they have a glass transition temperature which is well below room temperature.

The block character of the at least one amphiphilic polymer used herein consequently manifests itself by the existence of at least two glass transition temperatures (Tg), at least one Tg being greater and at least one other Tg being less than room temperature (20° C.).

The relatively more hydrophobic blocks of the at least one amphiphilic polymer may have, for example, a weight-average molecular mass ranging from 10 000 to 100 000, and the relatively more hydrophilic blocks of the at least one amphiphilic polymer may have a weight-average molecular mass, for example, ranging from 1000 to 100 000.

Each of the monomers forming the at least one polyfunctional unit (c), for example, comprises at least two polymerizable functional groups which have a different reactivity from each other. This difference in reactivity makes it possible to polymerize, in a first instance, only the most reactive functional groups and to preserve the less reactive functional groups which will serve, in a second instance, for the attachment of the relatively more hydrophilic sequence.

For example, the at least two polymerizable functional groups may be chosen, for example, from, vinyl, allyl, acryloyl and methacryloyl groups, the latter two having a considerably higher reactivity than the former.

For example, the at least one polyfunctional unit (c) may be derived, for example, from at least one monomer of the following formula:

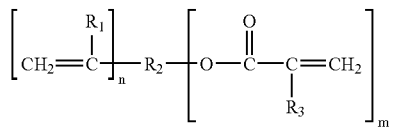

wherein
n and m, which may be identical or different, each range from 1 to 4,
the sum m+n is greater than or equal to 2,
$R_1$ and $R_3$, which may be identical or different, are each chosen from a hydrogen atom, and $C_1$-$C_{22}$ alkyl groups, for example, $C_1$-$C_3$ alkyl groups,
$R_2$ is chosen from $C_1$-$C_{22}$ alkylene groups, $C_3$-$C_6$ cycloalkylene groups, $C_6$-$C_{18}$ arylene groups, $C_7$-$C_{24}$ alkylarylene groups, —$(CH_2$—$CH_2$—$O)_p$ groups wherein p ranges from 1 to 50, $(CH_2(CH_3)$—$CH_2$—$O)_p$ groups wherein p ranges from 1 and 50, amido groups, ester groups, polyamido groups, and polyester groups.

For example, the at least one polyfunctional unit (c) may be derived from at least one monomer chosen from allyl methacrylate, allyl acrylate, vinyl methacrylate, vinyl acrylate, vinylacrylamide, vinylmethacrylamide, allylmethacrylamide, allylacrylamide. In one embodiment, the at least one polyfunctional unit (c) is derived from allyl methacrylate.

In one embodiment, the at least one amphiphilic polymer consists essentially of the units (a), (b) and (c) as described above.

The proportions of the units (a), (b) and (c) in the at least one amphiphilic polymer are, for example:
(a) at least one anionic unit: ranging from 5 to 95 mol %, for example, from 5 to 50 mol %,
(b) at least one nonionic unit: ranging from 5 to 70 mol %, for example, from 10 to 70 mol %,
(c) at least one polyfunctional unit: ranging from 0.005 to 2 mol %, for example, from 0.1 to 1.5 mol %.

In one embodiment, the at least one amphiphilic polymer consists essentially of:
(a) nonionic units derived from butyl acrylate,
(b) anionic units derived from methacrylic acid and acrylic acid, and
(c) bifunctional units derived from allyl methacrylate, and, wherein, for example, the at least one amphiphilic polymer comprises from 27.5 to 30.5 mol % of butyl acrylate, from 26 to 36 mol % of acrylic acid, from 33.3 to 45.3 mol % of methacrylic acid and from 0.48 to 0.92 mol % of allyl methacrylate.

For example, the copolymer FIXATE® G100 by the company NOVEON may be used.

The compositions disclosed herein may, for example, comprise from 0.01 to 10% by weight, for example, from 0.1 to 5% by weight, relative to the total weight of the composition, of the at least one amphiphilic polymer.

The composition disclosed herein further comprises, in addition to the at least one amphiphilic polymer described above, at least one cationic polymer.

The expression "at least one cationic polymer" means any polymer comprising cationic groups and/or groups which can be ionized into cationic groups.

The at least one cationic polymer is chosen from all those already known per se for their capacity to improve the cosmetic properties of hair treated with detergent compositions. For example, those described in patent applications EP 0 337 354, FR 2 270 846, FR 2 383 660, FR 2 598 611, FR 2 470 596 and FR 2 519 863 may be used.

For example, the at least one cationic polymer can be chosen from those comprising units comprising at least one amine group chosen from primary, secondary, tertiary and quaternary amine groups which may either form part of the principal polymer chain, or which may be carried by a side functional group directly linked to the principal polymer chain.

The at least one cationic polymer may be chosen, for example, from polymers of the polyamine, polyaminoamide and poly(quaternary ammonium) type. These polymers are known in the art.

The polymers of the polyamine, polyaminoamide and poly(quaternary ammonium) type, which can be used in the composition disclosed herein, are those described in French Patent Nos. 2 505 348 and 2 542 997. For example, these polymers can be chosen from the following families of polymers:

(1) The homopolymers and copolymers derived from acrylic and methacrylic esters and amides and comprising at least one unit chosen from units of the following formulae:

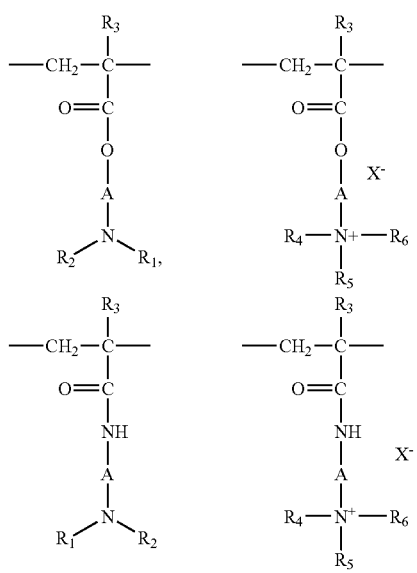

wherein:

R$_3$, which may be identical or different, is chosen from a hydrogen atom and a CH$_3$ radical;

A, which may be identical or different, is chosen from linear and branched alkyl groups comprising from 1 to 6 carbon atoms, for example, 2 or 3 carbon atoms and hydroxyalkyl groups comprising from 1 to 4 carbon atoms;

R$_4$, R$_5$, R$_6$, which may be identical or different, are each chosen from alkyl groups comprising from 1 to 18 carbon atoms, for example, alkyl groups comprising from 1 to 6 carbon atoms, and benzyl radicals;

R$_1$ and R$_2$, which may be identical or different, are each chosen from a hydrogen atom and alkyl groups comprising from 1 to 6 carbon atoms, for example, methyl and ethyl groups;

X$^-$ is an anion chosen from anions derived from inorganic and organic acids such as a methosulphate anion and halides such as chloride and bromide.

The copolymers of the family (1) may further comprise at least one unit derived from comonomers which may be chosen from acrylamides, methacrylamides, diacetone acrylamides, acrylamides and methacrylamides substituted on the nitrogen with at least one group chosen from lower (C$_1$-C$_4$) alkyls groups, groups derived from acrylic acids, methacrylic acids, acrylic esters, methacrylic esters and vinyllactam groups such as vinylpyrrolidone and vinylcaprolactam, and vinyl esters.

Thus, the copolymers of the family (1) may be chosen, for example, from:

the copolymers of acrylamide and dimethylaminoethyl methacrylate quaternized with dimethyl sulphate or with a dimethyl halide such as that sold under the name HERCOFLOC® by the company HERCULES, the copolymers of acrylamide and methacryloyloxyethyltrimethylammonium chloride described, for example, in Patent Application EP A 080976 and sold under the name BINAQUAT® P 100 by the company CIBA GEIGY, the copolymer of acrylamide and methacryloyloxyethyltrimethylammonium methosulphate sold under the name RETEN® by the company HERCULES, the quaternized and nonquaternized vinylpyrrolidone/dialkylaminoalkyl acrylate or methacrylate copolymers, such as the products sold under the name GAFQUAT® by the company ISP, for example, GAFQUAT® 734 or GAFQUAT® 755 and the products called COPOLYMER 845, 958 and 937. These polymers are described in detail in French Patent Nos. 2,077,143 and 2,393,573, the dimethylaminoethyl methacrylate/vinyl-caprolactam/vinylpyrrolidone terpolymers such as the product sold under the name GAFFIX® VC 713 by the company ISP, the vinylpyrrolidone/methacrylamidopropyidimethylamine copolymers marketed, for example, under the name STYLEZE® CC 10 by ISP, and the quaternized vinylpyrrolidone/dimethylaminopropyl methacrylamide copolymers such as the product sold under the name GAFQUAT® HS 100 by the company ISP.

(2) The cellulose ether derivatives comprising quaternary ammonium groups, described in French Patent No.1 492 597, for example, the polymers marketed under the names JR (JR 400, JR 125, JR 30M) and LR (LR 400, LR 30M) by the company AMERCHOL. These polymers are also defined in the CTFA dictionary as hydroxyethyl cellulose quaternary ammoniums which have reacted with an epoxide substituted by a trimethylammonium group.

(3) The cationic cellulose derivatives such as cellulose copolymers and cellulose derivatives grafted with a quaternary ammonium water-soluble monomer, and described, for example, in U.S. Pat. No. 4,131,576, such as hydroxyalkyl celluloses such as hydroxymethyl, hydroxyethyl and hydroxypropyl celluloses grafted, for example, with a salt chosen from methacryloylethyltrimethylammonium, methacrylamidopropyltrimethyl-ammonium and dimethyidiallylammonium salts. The marketed products corresponding to this definition are, for example, the products sold under the name Celquat® L 200 and Celquat® H 100 by the company National Starch.

(4) The cationic polysaccharides described, for example, in U.S. Pat. Nos. 3,589,578 and 4,031,307 such as guar gums comprising cationic trialkylammonium groups. Guar gums modified with a 2,3-epoxypropyltrimethylammonium salt (e.g. chloride) are, for example, used. Such products are marketed, for example, under the trade names JAGUAR® C13 S, JAGUAR® C 15, JAGUAR® C 17 or JAGUAR® C162 by the company RHODIA.

(5) Polymers comprising piperazinyl units and divalent groups chosen from alkylene and hydroxyalkylene divalent groups with straight and branched chains, optionally interrupted by at least one entity chosen from oxygen, sulphur and nitrogen atoms and aromatic and heterocyclic rings, and the oxidation and quaternization products of these polymers. Such polymers are described, for example, in French Patent Nos. 2,162,025 and 2,280,361.

(6) Water-soluble polyaminoamides prepared, for example, by polycondensation of an acid compound with a polyamine; these polyaminoamides may be crosslinked with at least one entity chosen from epihalohydrins, diepoxides, dianhydrides, unsaturated dianhydrides, diunsaturated derivatives, bishalohydrins, bisazetidiniums, bishaloacyldiamines, alkylbishalides, and oligomers resulting from the reaction of a difunctional compound which is reactive towards a bishalohydrin, a bisazetidinium, a bishaloacyldiamine, an alkylbishalide, an epihalohydrin, a diepoxide or a diunsaturated derivative. The crosslinking agent can be employed in proportions ranging from 0.025 to 0.35 mol per amine group of the polyaminoamide. These polyaminoamides may be alkylated or, if they comprise at least one tertiary amine functional group, they can be quaternized. Such polymers are described, for example, in French Patent Nos. 2,252, 840 and 2,368,508.

(7) Polyaminoamide derivatives resulting from the condensation of polyalkylenepolyamines with polycarboxylic acids, followed by an alkylation with difunctional agents. For example, the polyaminoamide derivatives are chosen from adipic acid/dialkylaminohydroxyalkyldialkylenetriamine polymers wherein the alkyl group comprises from 1 to 4 carbon atoms and, for example, is chosen from methyl, ethyl and propyl groups and alkylene groups comprising from 1 to 4 carbon atoms, for example, an ethylene group. Such polymers are described, for example, in French Patent No. 1,583, 363. Further, for example, the polyaminoamide derivatives may be chosen, for example, from the adipic acid/dimethylaminohydroxypropyl-diethylenetriamine polymers sold under the name Cartaretine® F, F4 and F8 by the company Sandoz.

(8) Polymers obtained by reaction of a polyalkylenepolyamine comprising two primary amine groups and at least one secondary amine group with a dicarboxylic acid chosen from diglycolic acids and saturated aliphatic dicarboxylic acids comprising from 3 to 8 carbon atoms. The molar ratio of the polyalkylenepolyamine to the dicarboxylic acid may range, for example, from 0.8:1 to 1.4:1. The polyaminoamide resulting therefrom may then be made to react with epichlorohydrin in a molar ratio of epichlorohydrin relative to the secondary amine group of the polyaminoamide ranging from 0.5:1 to 1.8:1. Such polymers are described, for example, in U.S. Pat. Nos. 3,227,615 and 2,961,347. Other non-limiting examples of such polymers include the adipic acid/epoxypropyl-diethylene-triamine copolymers marketed, for example, under the name Hercosett® 57 by the company Hercules Inc. and under the name of PD 170 or Delsette® 101 by the company Hercules.

(9) Cyclopolymers of alkyldiallylamine or of dialkyldiallylammonium, such as the homopolymers or copolymers comprising, as main constituent of the chain, at least one unit chosen from units corresponding to the formulae (Va) and (Vb):

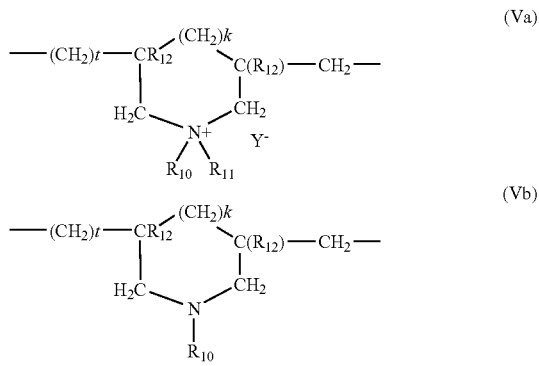

wherein k and t are equal to 0 or 1, the sum k+t being equal to 1;

$R_{12}$ is chosen from a hydrogen atom and a methyl group;

$R_{10}$ and $R_{11}$, which may be identical or different, are each chosen from alkyl groups comprising from 1 to 22 carbon atoms, $C_{1-5}$ hydroxyalkyl groups, and lower ($C_1$-$C_4$)-amidoalkyl groups or $R_{10}$ and $R_{11}$ may form, together with the nitrogen atom to which they are attached, a heterocyclic group such as piperidinyl and morpholinyl groups; and $Y^-$ is an anion chosen from bromide, chloride, acetate, borate, citrate, tartrate, bisulphate, bisulphite, sulphate and phosphate anions.

These polymers are described, for example, in French Patent No. 2,080,759 and in its Certificate of Addition 2,190,406.

For example, the cyclopolymers of alkyldiallylamine or of dialkyl-diallylammonium may be chosen from the dimethyldiallylammonium chloride homopolymer sold under the name MERQUAT® 100 by the company NALCO (and its homologues of low weight-average molecular mass) and the copolymers of diallyl-dimethylammonium chloride and acrylamide marketed under the name MERQUAT® 550.

(10) The quaternary diammonium polymers comprising repeat units corresponding to the formula (VI):

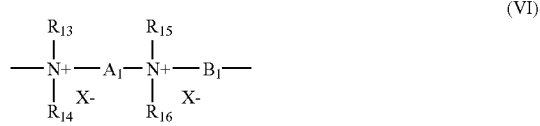

wherein:

$R_{13}$, $R_{14}$, $R_{15}$ and $R_{16}$, which may be identical or different, are each chosen from aliphatic, alicyclic and arylaliphatic groups comprising from 1 to 20 carbon atoms and from lower hydroxyalkyl aliphatic groups, or $R_{13}$, $R_{14}$, $R_{15}$ and $R_{16}$, together or separately, form, together with the nitrogen atoms to which they are attached, heterocycles optionally comprising a second heteroatom other than nitrogen, or $R_{13}$, $R_{14}$, $R_{15}$ and $R_{16}$ are each chosen from linear and branched $C_1$-$C_6$ alkyl groups substituted by at least one group chosen from nitrile, ester, acyl, amide and —CO—O—$R_{17}$-D and —CO—NH—$R_{17}$-D groups wherein $R_{17}$ is chosen from alkylene groups and D is chosen from quaternary ammonium groups;

$A_1$ and $B_1$, which may be identical or different, are each chosen from linear and branched, saturated and unsaturated, polymethylene groups comprising from 2 to 20 carbon atoms which may comprise, bonded to or inserted into the main chain, at least one entity chosen from aromatic rings, oxygen and sulphur atoms and sulphoxide, sulphone, disulphide, amino, alkylamino, hydroxyl, quaternary ammonium, ureido, amide and ester groups, and $X^-$ is an anion chosen from anions derived from inorganic and organic acids;

$A_1$, $R_{13}$ and $R_{15}$, may form, together with the two nitrogen atoms to which they are attached, a piperazine ring.

In addition, if $A_1$ is a group chosen from saturated and unsaturated, linear and branched alkylene and hydroxyalkylene groups, $B_1$ may also be chosen from the group:

$$—(CH_2)_n—CO-D-OC—(CH_2)_n—$$

wherein n ranges from 1 to 6, and D is chosen from:

a) a glycol residue of formula: —O-Z-O—, wherein Z is chosen from linear and branched hydrocarbon groups and a group corresponding to one of the following formulae:

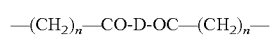
$$—(CH_2—CH_2—O)_x—CH_2—CH_2—$$

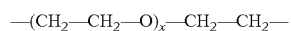
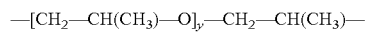
$$—[CH_2—CH(CH_3)—O]_y—CH_2—CH(CH_3)—$$

wherein x and y, which may be identical or different, are each chosen from an integer ranging from 1 to 4, representing a defined and unique degree of polymerization or any number ranging from 1 to 4 representing a mean degree of polymerization;

b) a disecondary diamine residue such as a piperazine derivative;

c) a diprimary diamine residue of formula: —NH—Y—NH—, where Y is chosen from linear and branched hydrocarbon groups and the divalent group —$CH_2$—$CH_2$—S—S—$CH_2$—$CH_2$—; and d) a ureylene group of formula —NH—CO—NH—.

In one embodiment, $X^-$ is an anion such as chloride and bromide.

These polymers have a number-average molecular mass which may range, for example, from 1000 to 100,000.

These polymers are described, for example, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, the polymers that comprise repeating units corresponding to the formula (VII) below can be used:

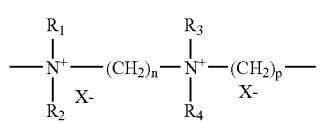

(VII)

wherein $R_1$, $R_2$, $R_3$ and $R_4$, which may be identical or different, are each chosen from alkyl and hydroxyalkyl groups comprising from 1 to 4 carbon atoms, n and p, which may be identical or different, are each an integer ranging from 2 to 20 and $X^-$ is an anion chosen from anions derived from inorganic and organic acids.

For example, one compound of formula (VII) can be used in the composition disclosed herein, wherein $R_1$, $R_2$, $R_3$ and $R_4$ are each a methyl group and n=3, p=6 and X=Cl, called hexadimethrine chloride (CTFA).

(11) Poly(quaternary ammonium) polymers comprising units of formula (VIII):

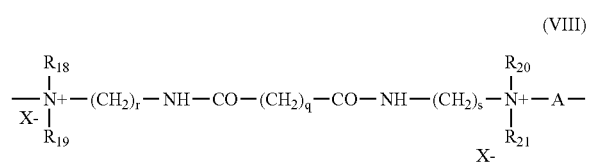

(VIII)

wherein:
$R_{18}$, $R_{19}$, $R_{20}$ and $R_{21}$, which may be identical or different, are each chosen from a hydrogen atom and methyl, ethyl, propyl, β-hydroxyethyl, β-hydroxypropyl and —$CH_2CH_2$(OCH$_2$CH$_2$)$_p$OH groups, wherein p is equal to 0 or to an integer ranging from 1 to 6, provided that $R_{18}$, $R_{19}$, $R_{20}$ and $R_{21}$ do not simultaneously denote a hydrogen atom,
r and s, which may be identical or different, are each an integer ranging from 1 to 6,
q is equal to 0 or to an integer ranging from 1 to 34,
$X^-$ is an anion such as a halide,
A is chosen from divalent radicals, for example, —$CH_2$—$CH_2$—O—$CH_2$—$CH_2$—.

Such polymers are described, for example, in European Patent Application EP A-122 324.

The poly(quaternary ammonium) polymers comprising units of formula (VIII) may be chosen, for example, from the products Mirapol® A 15, Mirapol® AD1, Mirapol® AZ1 and Mirapol® 175, sold by the company Miranol.

(12) Quaternary vinylpyrrolidone and vinylimidazole polymers such as the products marketed under the names Luviquat® FC 905, FC 550 and FC 370 by the company B.A.S.F. For example, the quaternary vinylpyrrolidone and vinylimidazole polymers may be chosen from vinylpyrrolidone and methylvinylimidazolium chloride copolymers.

(13) Polyamines such as the Polyquart H® sold by Cognis, under the name of "Polyethylene glycol (15) Tallow Polyamine" in the CTFA dictionary.

(14) Polymers, which may be crosslinked, of methacryloyloxy($C_1$-$C_4$ alkyl)tri($C_1$-$C_4$ alkyl)ammonium salts such as the polymers obtained by homopolymerization of dimethylaminoethyl methacrylate quaternized with methyl chloride, or by copolymerization of acrylamide and of dimethylaminoethyl methacrylate quaternized with methyl chloride, the homo- or copolymerization being followed by crosslinking with a compound comprising olefinic unsaturation, for example, methylenebisacrylamide. For example, it is possible to employ a crosslinked acrylamide/methacryloyloxyethyltrimethylammonium chloride copolymer (20/80 by weight) in the form of a dispersion comprising 50% by weight of the said copolymer in mineral oil. This dispersion is marketed under the name of SALCARE® SC 92 by the company CIBA. It is also possible to employ a crosslinked methacryloyloxy-ethyltrimethylammonium chloride homopolymer comprising approximately 50% by weight of the homopolymer in mineral oil or in a liquid ester. These dispersions are marketed under the names of SALCARE® SC 95 and SALCARE® SC 96 by the company CIBA.

The at least one cationic polymer that may be employed in the composition disclosed herein can be chosen, for example, from cationic proteins and hydrolysates of cationic proteins, polyalkyleneimines, such as polyethyleneimines, polymers comprising vinylpyridine and vinylpyridinium units, condensates of polyamines and of epichlorohydrin, quaternary polyureylenes and cationic chitin derivatives.

Additional non-limiting examples of the at least one cationic polymer include cellulose ether derivatives comprising quaternary ammonium groups such as the products sold under the name JR 400 by the company AMERCHOL, cationic cyclopolymers, for example, the homopolymers and copolymers of dimethyldiallylammonium chloride, sold under the names MERQUAT® 100, MERQUAT® 550 and MERQUAT® S by the company NALCO, cationic polysaccharides such as guar gums modified by a salt of 2,3-epoxypropyltrimethylammonium, quaternized copolymers of vinylpyrrolidone and vinylimidazole, polyquaternary ammonium polycondensates, for example, comprising the repeat units of formulae (VI) and (VIII) as indicated above, and mixtures thereof.

Even further, for example, the quaternized copolymers of vinylpyrrolidone and vinylimidazole may be used.

The concentration of the at least one cationic copolymer in the composition disclosed herein ranges, for example, from 0.001% to 10% by weight, further for example, from 0.05 to 5% by weight, and even further, for example, from 0.05 to 1% by weight, relative to the total weight of the composition.

The at least one anionic surfactant which can be used in the composition disclosed herein may, for example, be chosen from salts, for example, the alkali metal salts such as the sodium salts, the ammonium salts, the amine salts, the amino alcohol salts and the salts of alkaline-earth metals, for example salts of magnesium, of the following types: alkyl sulphates, alkyl ether sulphates, alkyl amidoether sulphates, alkyl aryl polyether sulphates, monoglyceride sulphates; alkyl sulphonates, alkyl amide sulphonates, alkyl aryl sulphonates, α-olefin sulphonates, paraffin sulphonates, alkyl sulphosuccinates, alkyl ether sulphosuccinates, alkyl amide sulphosuccinates, alkyl sulphoacetates, acyl sarcosinates and acyl glutamates, and the alkyl and acyl groups of all these compounds comprising from 6 to 24 carbon atoms, and aryl groups, such as phenyl and benzyl groups.

The at least one anionic surfactant may also be chosen, for example, from monoesters of $C_{6-24}$ alkyl and of polyglycoside dicarboxylic acids such as alkyl glucoside citrates, alkyl polyglycoside tartrates and alkyl polyglycoside sulphosuccinates, alkyl sulphosuccinamates, acyl isethionates and N-acyltaurates, and the alkyl and acyl groups of all these compounds comprising from 12 to 20 carbon atoms.

Surfactants of acyl lactylates wherein the acyl group comprises from 8 to 20 carbon atoms can also be used.

In addition, the at least one anionic surfactant can be chosen from alkyl-D-galactosideuronic acids and their salts and polyoxyalkylenated ($C_6$-$C_{24}$)alkyl ether carboxylic acids, polyoxyalkylenated ($C_6$-$C_{24}$)alkyl ($C_6$-$C_{24}$)aryl ether carboxylic acids, polyoxyalkylenated ($C_6$-$C_{24}$)alkyl amidoether carboxylic acids and their salts, for example, those comprising from 2 to 50 ethylene oxide units.

Further, for example, the at least one anionic surfactant chosen from alkyl sulphates, alkyl ether sulphates and alkyl ether carboxylates, for example, in the form of alkali and alkaline-earth metal, ammonium, amine and amino alcohol salts can be used.

It may be possible to introduce into the composition disclosed herein at least one additional surfactant chosen from amphoteric and nonionic surfactants.

The amphoteric surfactants which can be used in the composition disclosed herein may, for example, be chosen from secondary and tertiary aliphatic amine derivatives wherein the aliphatic group is chosen from linear and branched chains comprising from 8 to 22 carbon atoms and comprising at least one anionic group chosen from, for example, carboxylate, sulphonate, sulphate, phosphate and phosphonate groups. The amphoteric surfactants may be chosen, further, for example, from ($C_8$-$C_{20}$)alkylbetaines, sulphobetaines, ($C_8$-$C_{20}$)alkylamido-($C_2$-$C_8$)alkylbetaines and ($C_8$-$C_{20}$)alkylamido($C_2$-$C_8$)alkyl-sulphobetaines.

Among the amine derivatives, the products marketed under the name MIRANOL®, as described in the U.S. Pat. Nos. 2,528,378 and 2,781,354 and classified in the CTFA dictionary, $3^{rd}$ edition, 1982, under the names amphocarboxy-glycinate and amphocarboxypropionate having the respective structures (1) and (2) may be used:

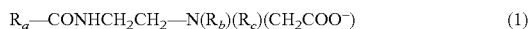

$$R_a\text{—CONHCH}_2\text{CH}_2\text{—N}(R_b)(R_c)(\text{CH}_2\text{COO}^-) \quad (1)$$

wherein:

$R_a$ is chosen from alkyl groups derived from an acid $R_a$—COOH present in hydrolysed copra oil, a heptyl, nonyl and undecyl group, $R_b$ is a beta-hydroxyethyl group, and $R_c$ is a carboxymethyl group; and

$$R_a'\text{—CONHCH}_2\text{CH}_2\text{—N(B)(C)} \quad (2)$$

wherein:

B is chosen from —$CH_2CH_2OX'$ groups,

C is chosen from —$(CH_2)_z$—Y' groups, wherein z=1 or 2,

X' is chosen from the group —$CH_2CH_2$—COOH and a hydrogen atom,

Y' is chosen from —COOH and the group —$CH_2$—CHOH—$SO_3H$, $R_a'$ is chosen from alkyl groups of an acid $R_a'$—COOH present in copra oil and in hydrolysed linseed oil, alkyl groups, such as a $C_{17}$ alkylgroup and its iso form, and an unsaturated $C_{17}$ group.

These compounds are classified in the CTFA dictionary, $5^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid.

For example, the cocoamphodiacetate marketed by the company RHODIA under the trade name MIRANOL® C2M concentrate may be used.

Among the amphoteric surfactants, ($C_8$-$C_{20}$ alkyl)betaines, ($C_8$-$C_{20}$ alkyl)amido($C_6$-$C_8$ alkyl)betaines, alkylamphodiacetates and mixtures thereof may, for example, be used.

The nonionic surfactants which can be used in the composition disclosed herein are compounds well known per se (see, for example, "Handbook of Surfactants" by M. R. PORTER, Blackie & Son publishing (Glasgow and London), 1991, pp 116-178). They are chosen, for example, from alcohols, alpha-diols, ($C_{1-20}$)alkylphenols and polyethoxylated, polypropoxylated and polyglycerolated fatty acids comprising a fatty chain comprising, for example, from 8 to 18 carbon atoms, it being possible for the number of ethylene oxide and propylene oxide groups to range, for example, from 2 to 50 and the number of glycerol groups to range, for example, from 2 to 30.

The non-ionic surfactants may also be chosen, for example, from copolymers of ethylene and propylene oxide, condensates of ethylene and propylene oxide with fatty alcohols; polyethoxylated fatty amides, for example, comprising from 2 to 30 ethylene oxide units, polyglycerolated fatty amides comprising on average from 1 to 5 glycerol groups and, for example, from 1.5 to 4, ethoxylated sorbitan fatty acid esters comprising from 2 to 30 ethylene oxide units, sucrose fatty acid esters, polyethylene glycol fatty acid esters, $C_6$-$C_{24}$ alkyl polyglycosides, N—($C_6$-$C_{24}$ alkyl)glucamine derivatives, amine oxides such as ($C_{10}$-$C_{14}$ alkyl)amine oxides and N—($C_{10}$-$C_{14}$ acyl)-aminopropylmorpholine oxides.

In one embodiment, among the nonionic surfactants cited above, $C_6$-$C_{24}$ alkyl polyglycosides are used.

As indicated above, the quantity of the at least one anionic surfactant is at least equal to 3% by weight, relative to the total weight of the composition. For example, the quantity of the at least one anionic surfactant may range from 5% to 35% by weight, and further, for example, from 8% to 25% by weight, relative to the total weight of the composition.

The total quantity of the at least one additional surfactant, when they are present, ranges, for example, from 0.5 to 30%, and, further for example, from 1 to 20% by weight, relative to the total weight of the composition.

The cosmetically acceptable aqueous medium may comprise water or a mixture of water and at least one cosmetically acceptable solvent such as $C_1$-$C_4$ lower alcohols, for example, ethanol, isopropanol, tert-butanol and n-butanol, alkylene glycols such as propylene glycol, polyol ethers, $C_5$-$C_{10}$ alkanes, acetone, methyl ethyl ketone, $C_1$-$C_4$ alkyl acetates such as methyl acetate, ethyl acetate and butyl acetate, dimethoxyethane and diethoxyethane.

The pH of the composition disclosed herein may range, for example, from 3 to 8, such as from 4 to 7.

The composition disclosed herein may also comprise at least one formulation additive chosen from associative and nonassociative, anionic, amphoteric, zwitterionic, nonionic and cationic, natural and synthetic, polymeric thickeners, nonpolymeric thickeners such as acids and electrolytes, pearlescent agents, opacifying agents, perfumes, mineral, vegetable oils and synthetic oils, fatty acid esters, volatile silicones, nonvolatile silicones, organomodified silicones, and non-organomodified silicones, colorants, preservatives and pH-stabilizing agents.

Persons skilled in the art will be careful to choose the at least one formulation additive and its quantity so that they do not damage the advantageous properties of the composition disclosed herein.

The at least one formulation additive may be present in the composition disclosed herein in a total quantity ranging from 0 to 20% by weight, relative to the total weight of the composition.

The composition disclosed herein may be in a form chosen from homogeneous solutions, suspensions, water-in-oil (W/O) emulsions, oil-in-water (O/W) emulsions and multiple emulsions, all having a fluid, a more or less thick, or a gel consistency.

For example, the composition disclosed herein may be packaged in the absence of propellants.

The composition disclosed herein may be provided in the form chosen from shampoos, bath and shower products, and make-up removing products. In one embodiment, the composition disclosed herein is a shampoo.

The following examples illustrate embodiments disclosed herein without, however, being limiting in nature.

EXAMPLE 1

The following shampoo composition was prepared:

| | |
|---|---|
| Sodium lauryl ether sulphate ($C_{12}/C_{14}$ at 70/30) comprising 2.2 mol of ethylene oxide | 10.5 g (a.s.)[a] |
| ($C_{8/16}$)alkyl polyglycoside (PLANTAREN ® 2000, from COGNIS) | 4.0 g (a.s.) |
| Oxyethylenated lauryl alcohol (2.5 EO units) | 1.0 g |
| Copolymer of vinylpyrrolidine and methylvinylimidazolium chloride (5/95) as a 40% aqueous solution (LUVIQUAT ® FC 905 (BASF)) | 0.1 g (a.s.) |
| Amphiphilic, branched, block copolymer of butyl acrylate, acrylic acid, methacrylic acid and allyl methacrylate as a 27% by weight aqueous solution (FIXATE ® G100 (NOVEON)) | 0.2 g (a.s.) |
| Crosslinked polyacrylic acid | 0.2 g |
| Distearyl ether | 1.5 g |
| Mixture of fatty alcohols comprising 76% of behenyl alcohol (NAFOL ® 1822 C (company CONDEA)) | 1.5 g |
| Citric acid | q.s. pH 5 |
| Sodium chloride | 1.5 g |
| Perfume, preservatives | q.s. |
| Demineralized water | q.s. 100 g |

[a] a.s. = active substance

This shampoo has good hair-styling properties (body, retention) and cosmetic properties, for example, sleekness and gloss.

EXAMPLES 2 and 3

The following shampoo compositions were prepared:

| Composition | Example 2 | Example 3 |
|---|---|---|
| Sodium lauryl ether sulphate (C12/C14 at 70/30) comprising 2.2 mol of ethylene oxide | 14 g A.S. | 10 g A.S. |
| Sodium/magnesium lauryl ether sulphate (80/20) comprising 4 mol of ethylene oxide | — | 3.1 g A.S. |
| Cocoamidopropylbetaine | 2.4 g A.S. | — |
| Sodium cocoamidoethyl (N-hydroxyethyl, N-carboxymethyl) glycinate, sold under the name Miranol C2M by the company RHODIA | — | 4.5 g A.S. |
| Hydroxypropylguar trimethylammonium chloride, sold under the name Jaguar C-162 by the company RHODIA | — | 0.25 g |
| Hydroxyethylcellulose crosslinked with epichlorohydrin, quaternized with trimethylamine, sold under the name JR 400 by the company AMERCHOL | 0.4 g | — |
| Branched block butyl acrylate/acrylic acid/methacrylic acid polymer as an aqueous solution comprising 27% A.S. provided under the name FIXATE G100 by the company NOVEON | 3.75 g | 3.75 g |
| Polydimethylsiloxane having a viscosity of 500 000 cst, sold under the name MIRASIL DM 500 000 by the company RHODIA | 1.5 g | — |
| Crosslinked polyacrylic acid | 0.2 g | 0.1 g |
| Monoisopropanolamide of copra acids | 1.2 g | 0.2 g |
| Behenyl alcohol | 1.5 g | — |
| Distearyl ether | 1.5 g | — |
| Ethylene glycol distearate | — | 2 g |
| Sodium hydroxide q.s. | pH 6.5 | |
| Citric acid q.s. | — | pH 6 |
| Perfume, preservatives | q.s. | q.s. |
| Demineralized water q.s. | 100 g | 100 g |

These compositions have good hair-styling properties (body, retention) and cosmetic properties, for example, on the criteria of disentanglement and gloss.

What is claimed is:

1. A cosmetic composition comprising, in a cosmetically acceptable medium,
    at least one amphiphilic branched block copolymer consisting of
    (a) from 27.5 to 30.5 mol % of butyl acrylate,
    (b) from 26 to 36 mol % of acrylic acid and from 33.3 to 45.3 mol % of methacrylic acid, and
    (c) from 0.48 to 0.92 mol % of allyl methacrylate,
    at least one cationic polymer, and
    at least 3% by weight, relative to the total weight of the composition, of at least one anionic surfactant.

2. The composition according to claim 1, wherein the at least one amphiphilic branched block copolymer has a structure comprising at least one hydrophilic block attached to at least one hydrophobic block, via allyl methacrylate.

3. The composition according to claim 1, wherein the at least one amphiphilic branched block copolymer has at least two glass transition temperatures (Tg) of which at least one is greater than room temperature (20° C.) and the other is less than room temperature.

4. The composition according to claim 1, wherein the concentration of the at least one amphiphilic branched block copolymer ranges from 0.01% to 10% by weight, relative to the total weight of the composition.

5. The composition according to claim 4, wherein the concentration of the at least one amphiphilic branched block copolymer ranges from 0.1 to 5% by weight, relative to the total weight of the composition.

6. The composition according to claim 1, wherein the at least one cationic polymer is chosen from cellulose ethers comprising quaternary ammonium groups, cationic cyclopolymers based on dimethyldiallylammonium chloride, cationic polysaccharides, quaternized polymers of vinylpyrrolidone and vinylimidazole and polycondensates of polyquaternary ammonium.

7. The composition according to claim 6, wherein the cationic polysaccharides are chosen from guar gums modified with a 2,3-epoxypropyltrimethylammonium salt.

8. The composition according to claim 1, wherein the at least one cationic polymer is present in an amount ranging from 0.001% to 10% by weight, relative to the total weight of the composition.

9. The composition according to claim 8, wherein the at least one cationic polymer is present in an amount ranging from 0.05 to 5% by weight, relative to the total weight of the composition.

10. The composition according to claim 9, wherein the at least one cationic polymer is present in an amount ranging from 0.05 to 1% by weight, relative to the total weight of the composition.

11. The composition according to claim 1, wherein the at least one anionic surfactant is chosen from alkyl sulphates, alkyl ether sulphates and alkyl ether carboxylates and mixtures thereof.

12. The composition according to claim 11, wherein the at least one anionic surfactant is chosen from alkali and alkaline-earth metal, ammonium, amine and amino alcohol salts of alkyl sulphates, alkyl ether sulphates and alkyl ether carboxylates.

13. The composition according to claim 1, wherein the concentration of the at least one anionic surfactant ranges from 5 to 35% by weight, relative to the total weight of the composition.

14. The composition according to claim 13, wherein the concentration of the at least one anionic surfactant ranges from 8 to 25% by weight, relative to the total weight of the composition.

15. The composition according to claim 1, further comprising at least one additional surfactant chosen from nonionic surfactants and amphoteric surfactants.

16. The composition according to claim 15, wherein the nonionic surfactants are chosen from $C_6$-$C_{24}$ alkyl polyglycosides.

17. The composition according to claim 15, wherein the amphoteric surfactants are chosen from ($C_8$-$C_{20}$ alkyl)betaines, ($C_8$-$C_{20}$ alkyl)amido($C_2$-$C_8$ alkyl)betaines, alkylamphodiacetates and mixtures thereof.

18. The composition according to claim 1, further comprising at least one formulation additive chosen from associative and nonassociative, anionic, amphoteric, zwitterionic, nonionic and cationic, natural and synthetic, polymeric thickeners, nonpolymeric thickeners, pearlescent agents, opacifying agents, perfumes, mineral, vegetable, and synthetic oils, fatty acid esters, volatile silicones, nonvolatile silicones, organomodified silicones, and non-organomodified silicones, colorants, preservatives and pH-stabilizing agents.

19. The composition according to claim 18, wherein the nonpolymeric thickeners are chosen from acids and electrolytes.

20. The composition according to claim 1, wherein the composition is provided in a form chosen from shampoos, bath and shower products, and make-up removing products.

21. The composition according to claim 20, wherein the composition is provided in the form of a shampoo.

22. A process for treating a keratinous material comprising applying to said keratinous material a composition comprising
at least one amphiphilic branched block copolymer consisting of
(a) from 27.5 to 30.5 mol % of butyl acrylate,
(b) from 26 to 36 mol % of acrylic acid and from 33.3 to 45.3 mol % of methacrylic acid, and
(c) from 0.48 to 0.92 mol % of allyl methacrylate, at least one cationic polymer, and
at least 3% by weight, relative to the total weight of the composition, of at least one anionic surfactant, and,
after an optional exposure time, rinsing the keratinous material.

23. The process according to claim 22, wherein the at least one amphiphilic branched block copolymer has a structure comprising at least one hydrophilic block attached to at least one hydrophobic block, via allyl methacrylate.

24. The process according to claim 22, wherein the optional exposure time ranges from 0 seconds to 30 minutes.

* * * * *